United States Patent
Machida et al.

(10) Patent No.: US 7,186,540 B2
(45) Date of Patent: Mar. 6, 2007

(54) THERMOSTABLE GLUTAMINASE AND THERMOSTABLE GLUTAMINASE GENE

(75) Inventors: Masayuki Machida, Ibaraki (JP); Keietsu Abe, Ibaraki (JP); Katsuya Gomi, Ibaraki (JP); Kiyoshi Asai, Tokyo (JP); Motoaki Sano, Ibaraki (JP); Taishin Kin, Tokyo (JP); Hideki Nagasaki, Tokyo (JP); Akira Hosoyama, Tokyo (JP); Osamu Akita, Hiroshima (JP); Naotake Ogasawara, Nara (JP); Satoru Kuhara, Fukuoka (JP); Kotaro Ito, Chiba (JP); Kenichiro Matsushima, Chiba (JP); Yasuji Koyama, Chiba (JP)

(73) Assignees: National Institute of Advanced Indusrtial Science and Technology, Tokyo (JP); National Institute of Technology and Evaluation, Tokyo (JP); National Research Institute of Brewing, Hiroshima (JP)

( * ) Notice: Subject to any disclaimer, the term of this patent is extended or adjusted under 35 U.S.C. 154(b) by 441 days.

(21) Appl. No.: 10/327,388

(22) Filed: Dec. 24, 2002

(65) Prior Publication Data

US 2004/0082053 A1    Apr. 29, 2004

(30) Foreign Application Priority Data

Dec. 27, 2001   (JP)   ............................. 2001-403261

(51) Int. Cl.
| | |
|---|---|
| C12N 9/80 | (2006.01) |
| C12N 5/00 | (2006.01) |
| C12N 15/00 | (2006.01) |
| C12N 1/20 | (2006.01) |
| C12N 1/00 | (2006.01) |
| C07H 21/04 | (2006.01) |
| C12P 21/06 | (2006.01) |
| C07K 14/00 | (2006.01) |
| C12N 9/78 | (2006.01) |

(52) U.S. Cl. .................. 435/228; 435/227; 435/320.1; 435/69.1; 435/252.3; 435/325; 435/254.11; 435/254.2; 536/23.1; 536/23.2; 530/350

(58) Field of Classification Search ............... 435/227, 435/228, 320.1, 252.3, 325, 69.1, 254.11, 435/254.2; 536/23.1, 23.2; 530/350
See application file for complete search history.

(56) References Cited

U.S. PATENT DOCUMENTS

| | | | | |
|---|---|---|---|---|
| 6,541,236 | B2 * | 4/2003 | Ito et al. | ............ 435/227 |
| 6,881,565 | B2 * | 4/2005 | Ito et al. | ............ 435/227 |
| 6,919,195 | B2 * | 7/2005 | Matsushima et al. | ....... 435/227 |

FOREIGN PATENT DOCUMENTS

| | | |
|---|---|---|
| EP | 1 077 256 A1 | 2/2001 |
| JP | 2000-166547 | 6/2000 |
| JP | 2002-218986 | 8/2002 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Guo et al., PNAS 101(25):9205-9210, 2004.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E. R., Molecular Biotechnology 7:253-265, 1997.*
Phillips, A., J. Pharm. Pharmacology 53:1169-1174, 2001.*
Gardlik et al., Med. Sci. Monit. 11(4):RA110-121, 2005.*
Thammarongtham et al., J. Mol. Microbiol. Biotechnol. 3(4):611-617, 2001.*
Thammarongtham et al., EMBL accession No. AY005477, 2000.*
Thammarongtham et al., EMBL accession No. AAG02575, 2000.*
Koibuchi et al., Appl. Microbiol. Biotechnol. 54:59-68, Jul. 2000.*
Koibuchi et al., EMBL accession No. BAA86934, 2000.*
Koibuchi et al., EMBL accession No. AB029552, 2000.*
Yano et al., "Purification and Properties of Glutaminase from *Aspergillus oryzae*", J. Ferment. Technol., vol. 66, No. 2, pp. 137-143, (1988).

* cited by examiner

*Primary Examiner*—Delia M. Ramirez
(74) *Attorney, Agent, or Firm*—Finnegan, Henderson, Farabow, Garrett, & Dunner, L.L.P.

(57) ABSTRACT

A completely novel glutaminase is provided: (a) a protein consisting of an amino acid sequence represented by SEQ ID NO: 2, or (b) a protein consisting of an amino acid sequence derived from the amino acid sequence represented by SEQ ID NO: 2 by deletion, substitution or addition of one or more amino acids, and possessing glutaminase activity. This protein is a novel glutaminase possessing excellent thermostability and the like.

12 Claims, 2 Drawing Sheets

THERMOSTABLE GLUTAMINASE AND THERMOSTABLE GLUTAMINASE GENE

FIELD OF THE INVENTION

The present invention relates to a glutaminase, a glutaminase gene, a recombinant DNA and a method for producing the glutaminase.

BACKGROUND OF THE INVENTION

Glutaminase (L-Glutamine amidohydrolase, EC3.5.1.2, hereinafter, referred to as glutaminase) is an enzyme that hydrolyzes glutamine into glutamic acid and ammonia. Glutaminase is known to play an important role in the food-processing industry, particularly when food flavorings, such as soy sauce, which is obtained by enzymatic degradation of protein, are produced. When soy sauce is produced, a protein, as a raw material, is degraded into peptides and finally into constitutive amino acids by the action of various proteinases produced by *Aspergillus*. Glutamic acid, which is a kind of constitutive amino acid, plays a central role among flavor-components of soy sauce. Two pathways have been devised to generate glutamic acid in soy sauce manufacture. One pathway is the direct generation of glutamic acid in the above described degradation process of the protein raw material (1st pathway) and the second pathway is the generation of glutamic acid by converting the glutamine produced in the degradation process of the protein raw material into glutamic acid by the action of glutaminase (2nd pathway). Protein-storing plants including soya beans that are the raw materials in soy sauce manufacture are rich in acidic amino acid, such as glutamic acid and asparatic acid. Most acidic amino acids are known to exist in the form of amide, such as glutamine and asparagine. In addition, glutamine generated by the degradation of raw materials in the soy sauce brewing process changes non-enzymatically and relatively quickly into tasteless pyroglutamic acid. Therefore, in soy sauce brewing, primary importance has been placed on the reaction which converts glutamine into glutamic acid (the 2nd pathway).

In soy sauce manufacture, the use of yellow koji molds (e.g. *Aspergillus sojae*) capable of high production of glutaminase has been shown to cause increases in the amount of glutamic acid in soy sauce moromi, which is formed after the raw material for soy sauce production is treated before fermentation (see Yamamoto et. al. J. Ferment. Technol., Vol. 52, No. 8, 564–569 (1974)), and that within this soy sauce moromi, there exists a correlation between the glutaminase in the insoluble fractions (also described as fractions of cell surface and cell first-surface, intracellular fractions, fractions of microbial body surface and fractions within the microbial body) of yellow koji molds and glutamic acid (see Nippon Shoyu Kenkyusho Zasshi Vol. 5, No. 1, 21–25, 1979). Thus, the glutaminase produced by koji molds has been recognized as important.

*Aspergilli* (including yellow koji molds) *Aspergillus oryzae* and *Aspergillus sojae*, have traditionally been used in the production of brewed food in Japan, such as miso, soy sauce and old-fashioned sake. These microbes are particularly important industrially, because of their high productivity of enzymes and high reliability of safety as attested by their long-standing use.

Some of the glutaminases produced by the microbes of the genus *Aspergillus* including these yellow koji molds have been purified and their properties reported. Intra- and extra-microbial glutaminases have also been purified from *Aspergillus oryzae* and their properties studied (see Yano, T et al, J. Ferment. Technol., Vol. 66, No. 2, 137–143 (1988)). All of these glutaminases have molecular weights of approximately 113,000 and they all have similar properties. Further, 2 types of extra-microbial glutaminases, which are different from the above types, have been purified from *Aspergillus oryzae*, and their properties have been studied (see WO99/60104, and JP Patent Publication (Unexamined Application) No. 2002-218986). The genes of these extra-microbial glutaminases have been isolated and analyzed. Further, extra-microbial glutaminases have been purified from *Aspergillus sojae* and their genes have been reported (see JP Patent Publication (Unexamined Application) No. 2000-166547). Furthermore, a glutaminase gene which is different from the above genes has also been isolated from *Aspergillus sojae* (see Japanese Patent Application No. 2001-187433).

The localization of the glutaminase of yellow koji molds has been studied. Fractions from 3 broadly classified locations: extracellular, cell surface and intracellular (cell membrane and cytoplasm), have been studied for their properties and distribution ratios using crude enzyme solutions. As a result, it has been reported that most glutaminases are located on the cell surface and intracellularly (see Nippon Shoyu Kenkyusho Zasshi Vol. 11, No. 3, 109–114, 1985).

Glutaminases derived from yellow koji molds and glutaminase genes that have been reported so far are all extra-microbial glutaminases. Based on analysis of molecular weight and enzymatic properties, however, it has been suggested that the only intra-microbial glutaminase, as the one obtained by Yano et al., may be identical to extra-microbial glutaminase. No glutaminase and genes thereof shown to be located definitely on the cell surface and intracellularly have been reported. As described above, insoluble glutaminase is known to have an effect in soy sauce manufacture, so that isolation of these glutaminases is strongly desired. Further, the use of these glutaminases has been limited in terms of industrial use, because of their low quantity of production and the like. Hence, isolation of the gene that enables mass-preparation of such glutaminases is also strongly desired.

Among the production methods for food flavorings involving enzymatic degradation of proteins, an extremely effective and efficient method for efficiently producing food flavorings having rich glutamic acid content involves the degradation of proteins at high temperature, because high temperature enhances the degradation rate of protein and prevents contamination by saprophytes. However, as the temperature rises, the efficiency of glutamine to pyroglutamic acid conversion also increases, glutaminase thus must act quickly. Therefore, high optimal temperature and thermostability are required for glutaminase to be utilizable under such conditions. Hence, isolation of glutaminase having these properties has been strongly desired.

SUMMARY OF THE INVENTION

Consequently, an object of the present invention is to provide a completely novel glutaminase, a glutaminase gene, a recombinant DNA and a method for producing the glutaminase, in particular, to provide a glutaminase with excellent thermastability, a gene of the glutaminase with excellent thermostability, a recombinant DNA and a method for producing the glutaminase with excellent thermostability.

As a result of intensive studies to attain the above objectives, we have completed the present invention by succeeding in cloning a novel glutaminase gene from yellow koji molds. That is, the present invention is:

1. A protein, which is the following (a) or (b):

(a) a protein consisting of an amino acid sequence represented by SEQ ID NO: 2;

(b) a protein consisting of an amino acid sequence derived from the amino acid sequence represented by SEQ ID NO: 2 by deletion, substitution or addition of one or more amino acids, and possessing glutaminase activity.

2. A protein or a partial fragment thereof, which consists of an amino acid sequence having 70% or more sequence homology with the full length amino acid sequence represented by SEQ ID NO: 2, and possesses glutaminase activity.

3. A glutaminase gene, which encodes the following protein (a) or (b):

(a) a protein consisting of the amino acid sequence represented by SEQ ID NO: 2;

(b) a protein consisting of an amino acid sequence derived from the amino acid sequence represented by SEQ ID NO: 2 by deletion, substitution or addition of one or more amino acids, and possessing glutaminase activity.

4. A glutaminase gene, which encodes a protein or a partial fragment thereof consisting of an amino acid sequence having 70% or more sequence homology with the full length amino acid sequence represented by SEQ ID NO: 2, and possesses glutaminase activity.

5. A glutaminase gene, which consists of the following DNA (a) or (b);

(a) a DNA consisting of a nucleotide sequence represented by SEQ ID NO: 1;

(b) a DNA hybridizing under stringent conditions to a DNA comprising a nucleotide sequence that is complementary to the DNA consisting of the nucleotide sequence represented by SEQ ID NO: 1, and encoding a protein possessing glutaminase activity.

6. A recombinant DNA, wherein the gene of the above 3, 4 or 5 is inserted to a vector DNA.

7. A transformant or a transductant, which comprises the recombinant DNA of the above 6.

8. A method for producing glutaminase, which comprises culturing the transformant or transductant of the above 7 in a medium, and collecting glutaminase from the culture product.

In addition, in the present invention, the nucleotide sequence represented by SEQ ID NO: 1 and the amino acid sequence represented by SEQ ID NO: 2 are identical to SEQ ID NOS: 13493 and 13494, respectively, in the specification of prior application No. 2001-403261 (filing date: Dec. 27, 2001).

The present invention is described in detail as follows.

To clone a glutaminase gene or a gene that contains the glutaminase gene and encodes a protein possessing glutaminase (enzyme) activity (hereinafter, may also be simply referred to as "the glutaminase gene"), we searched the genome sequence database of a yellow koji mold, *Aspergillus oryzae* strain RIB40, to identify a gene having a nucleotide sequence differing from that of the conventionally known glutaminase gene. Yellow koji molds were cultured in various media and the gene expression was studied. We found the gene that was expressed in microbial bodies cultured in bran media, and then cloned cDNA from RNA extracted from the microbial bodies. The full length ORF of the obtained cDNA was inserted into a yeast expression plasmid vector (pYES2.1/V5-His-TOPO®), and then the functions were analyzed using yeast (INVSc) which were transformed by the plasmid. As a result, this cDNA was confirmed to encode glutaminase, and we succeeded in mass-producing glutaminase derived from the gene product.

1. Glutaminase of the Present Invention

The glutaminase of the present invention is a protein comprising the amino acid sequence represented by SEQ ID NO: 2. For example, the enzyme can be purified from the culture product of yellow koji molds, such as *Aspergillus sojae* or *Aspergillus oryzae*. In addition, the enzyme can be obtained by allowing the glutaminase gene that has been cloned from the above yellow koji molds and the like to be expressed in an appropriate host vector system.

The glutaminase of the present invention may comprise an amino acid sequence derived from the amino acid sequence represented by SEQ ID NO: 2 by deletion, substitution or addition of one or more amino acids, as long as it possesses enzyme activity. Here, the term "(one or) more amino acids" means normally 2 to 300 amino acids, preferably 2 to 170 amino acids, more preferably 2 to 50 amino acids, and most preferably 2 to 10 amino acids. The number of amino acids varies depending on the positions or types of amino acid residues in the three-dimensional structure of a glutaminase protein. Further, as long as the protein possesses glutaminase activity, it may be a protein or a partial fragment thereof which comprises an amino acid sequence showing 70% or more, preferably 75% or more, more preferably 80% or more, and most preferably 85% or more sequence homology with the full length amino acid sequence represented by SEQ ID NO: 2.

To determine sequence homology between the two amino acid sequences or nucleotide sequences, sequences are pretreated to reach an optimum state for comparison. For example, the alignment with one sequence is optimized by inserting a gap into the other sequence. Afterwards, amino acid residues or nucleotides of each site are compared. When an amino acid residue or a nucleotide at a site of the first sequence is identical to an amino acid residue or a nucleotide at a corresponding site of the second sequence, these sequences are identical to each other at that site. Sequence homology between two sequences is expressed as a percentage of the number of sites identical between sequences to the total number of sites (all the amino acids or nucleotides).

According to the above principle, sequence homology between two amino acid sequences or nucleotide sequences is determined by the algorithm of Karlin and Altschul (Proc. Natl. Acad. Sci. USA 87:2264–2268, 1990 and Proc. Natl. Acad. Sci. USA 90:5873–5877, 1993). The BLAST program using such an algorithm was developed by Altschul et al (J. Mol. Biol. 215:403–410, 1990). Further, the Gapped BLAST is a program with higher sensitivity to determine sequence homology compared to the BLAST (Nucleic Acids Res. 25:3389–3402, 1997). The Gapped BLAST program is mainly used to search databases for sequences showing high sequence homology with a given sequence. These programs are available on the website of the National Center for Biotechnology Information (USA) on the Internet.

To express sequence homology between sequences, values determined using BLAST 2 Sequences software (FEMS Microbiol Lett., 174:247–250, 1999) developed by Tatiana A. Tatusova et al., are used in the present specification. This software is available and also obtainable on the website of the National Center for Biotechnology Information (USA) on the Internet. Programs and parameters used herein are as follows. In the case of amino acid sequences, the blastp program is used, and Open gap: 11 and extension gap: 1 penalties, gap x#dropoff: 50, expect: 10, word size: 3 and Filter: ON are used as parameters. In the case of nucleotide sequences, the blastn program is used, and Reward for a match: 1, Penalty for a mismatch: −2, Strand option: Both strands, Open gap: 5 and extension gap: 2 penalties, gap x#dropoff: 50, expect: 10, word size: 11 and Filter: ON are used as parameters. All of these parameters are used as default values on the web site.

However, when a sequence showing significant sequence homology is not found using the above BLAST software, a sequence showing some sequence homology can be further searched from databases using the high sensitivity FASTA software (W. R. Pearson and D. J. Lipman, Proc. Natl. Acad. Sci., 85:2444–2448, 1988). FASTA software can be used, for example, on the web site of the genome net. In this case, default values are also used as parameters. For example, when a search is performed for a nucleotide sequence, nr-nt is used as a database and the ktup value in this case is 6. In any cases, when a 30% or more, 50% or more, or 70% or more overlap of the whole is not shown, functional correlation cannot be necessarily be assumed. Thus, such values are not used as values showing sequence homology between two sequences.

The above respective methods are used to search for a sequence showing sequence homology mainly from databases. In the present invention, homology analysis can be employed using GENETYX® WIN Ver.5 (GENETYX®) as a means of determining sequence homology of individual sequences. This method is based on the Lipman-Pearson method (Science, 227: 1435–1441, 1985) which is frequently used as a high-speed and high-sensitivity method. When sequence homology of nucleotide sequences is analyzed, regions encoding proteins (CDS or ORF) are used, if possible. Unit Size to compare=2 and Pick up Location=5 are entered as parameters, and results are indicated with %. The sequence homology of an alignment showing the highest percentage point is used as a result. When a 30% or more, 50% or more, or 70% or more overlap with a query sequence is not shown, functional correlation is not necessarily assumed. Thus, the result is not used as a value showing sequence homology between two sequences. For example, even if there is a completely matched region of about several nucleotides/residues, this may likely be a mere random chance result. Moreover, in case of a match of several % in length of the whole, even when a particularly functional motif is contained, it is difficult to determine that the two sequences exhibit the same function as with the whole.

Specifically, when homology search is performed for the amino acid sequence represented by SEQ ID NO: 2 using each of the above methods, the highest sequence homology among those of known glutaminases is about 36% (a glutaminase derived from *Cryptococcus nodaensis*, JP Patent Publication (Unexamined Application) No. 2002-262887). Thus, a glutaminase comprising the amino acid sequence represented by SEQ ID NO: 2 can be said to be completely novel.

2. Cloning of Glutaminase Gene

The glutaminase gene of the present invention can be obtained from, for example, yellow koji molds, such as *Aspergillus sojae* or *Aspergillus oryzae*, other filamentous fungi, or other fungi. More specifically, an example is *Aspergillus oryzae* strain RIB40 (*Aspergillus oryzae* var. *viridis* Murakami, anamorph; ATCC42149). Total RNA is collected by conventional techniques from the culture product obtained by culturing these microbes in media under conditions for producing glutaminase. An example of a medium that can be used herein is a bran medium prepared by adding 2.22 g of deionized water to 2.78 g of wheat bran, and then auto-claved at 121° C. for 50 minutes. After culturing in the above medium for an appropriate time period, for example, for 30 hours, an appropriate amount of the culture product (for example, 1 g) is transferred into a mortar filled with liquid nitrogen and crushed with a pestle. The total RNA is then prepared using the method by Cathala et al. (DNA, 2 (4): 329–335, 1983).

RT-PCR is performed using the thus obtained total RNA as a template. As primers, any combination of primers may be employed, as long as it allows the amplification of the glutaminase gene of the present invention. For example, oligonucleotides having sequences of SEQ ID NO: 7 and SEQ ID NO: 8, respectively, can be used. For example, RT-PCR can be performed by conventional methods using a commercially available kit, such as a RNA LA-PCR Kit (TAKARA SHUZO). The resulting DNA containing the glutaminase gene of the present invention can be inserted into, for example, a plasmid vector, such as pCR2.1-TOPO® or pYES2.1/V5-His-TOPO® (both manufactured by INVITROGEN™). The nucleotide sequence of the thus obtained DNA can be determined by Sanger's method using commercially available reagents and a DNA sequencer. Examples of the thus obtained DNA containing the glutaminase gene of the present invention and the amino acid sequence of the glutaminase encoded by this gene are exemplified in SEQ ID NO: 1 (SEQ ID NO: 13493 of prior application No. 2001-403261) and SEQ ID NO: 2 (SEQ ID NO: 13494 of prior application No. 2001-403261), respectively.

In addition to the above genes, the glutaminase gene of the present invention may be a gene encoding a protein which comprises an amino acid sequence derived from the amino acid sequence represented by SEQ ID NO: 2 by deletion, substitution or addition of one or more amino acids, as long as the protein possesses glutaminase activity. In addition to selection by hybridization to be described later, such a gene can also be obtained by various known method for introducing mutations.

The glutaminase gene of the present invention can also be obtained by a selection method using hybridization, as described below. Examples of a gene source include yellow koji molds, such as *Aspergillus sojae* or *Aspergillus oryzae*. From these organisms, RNA or genomic DNA is prepared by conventional methods, and then inserted into a plasmid or phage, thereby preparing libraries. Next, nucleic acids to be used as probes are labeled by any method according to the detection method to be used. A nucleic acid that may be used as a probe has a length with which sufficient specificity can be obtained. For example, such a nucleic acid contains a part of or the whole sequence of SEQ ID NO: 1, that is, it contains at least 100 bases or more, preferably 200 bases or more, more preferably 450 bases or more, and most preferably 700 bases or more of the sequence of SEQ ID NO: 1. Subsequently, clones that hybridize under stringent conditions to labeled probes are selected from the above libraries. Regarding hybridization, when plasmid libraries are used, colony hybridization can be performed, and when phage libraries are used, plaque hybridization can be performed. The term "stringent conditions" means conditions wherein signals caused by specific hybrids are clearly distinguishable from that of non-specific hybrids. The stringent conditions vary depending on the hybridization system, the type, sequence and length of probes to be used herein. Such conditions can be determined by changing the temperature for hybridization and varying the temperature for washing and salt concentrations. For example, when the signals caused by non-specific hybrids are also strongly detected, specificity can be enhanced by elevating the temperature for hybridization and washing, and if necessary, lowering the salt concentration for washing. In addition, when the signals caused by specific hybrids are not also detected, hybrids can be stabilized by lowering the temperature for hybridization and washing, and if necessary, increasing the salt concentration for washing. Such an optimization can be easily performed by researchers in this technical field.

Under specific examples of the stringent conditions, hybridization is performed overnight (8 to 16 hours) using 5×SSC, blocking agent (Boehringer Mannheim) for 1.0% (W/V) nucleic acid hybridization, 0.1% (W/V) N-lauroyl sarcosine and 0.02% (W/V) SDS, and then washing is performed twice, for 15 minutes each, using 0.5×SSC and 0.1% (W/V) SDS, and preferably, using 0.1×SSC and 0.1% (W/V) SDS. The temperature for hybridization and washing is 52° C. or more, preferably 57° C. or more, more preferably 62° C. or more, and most preferably 67° C. or more.

Further, a nucleotide sequence is considered to encode a protein possessing activity substantially equivalent to that of the glutaminase of the present invention, when it shows 75% or more, preferably 80% or more, further preferably 85% or more, and most preferably 90% or more sequence homology with a 500 nucleotide or more part of or the whole nucleotide sequence of SEQ ID NO: 1.

DNA showing the above-described sequence homology in the nucleotide sequence, or showing that in the coding amino acid sequence can be obtained using hybridization as an indicator as described above. Alternatively, for example, such DNA can also be found easily from DNA groups having unknown functions that have been obtained by genomic nucleotide sequence analysis or the like or from public databases, for example by a search using the BLAST program described above. Such search methods are routinely employed by researchers in this technical field.

That the thus obtained DNA encodes a protein possessing glutaminase activity can be confirmed by, to be described later in "5. Production of glutaminase," incorporating DNA into an appropriate vector, transforming an appropriate host, culturing the transformant, and then measuring glutaminase activity.

3. Construction of Recombinant Vector

The recombinant vector of the present invention can be obtained by ligating the glutaminase gene of the present invention into an appropriate vector. Any vector that allows the production of glutaminase in a host to be transformed can be used. For example, plasmids, cosmids, phages, viruses, chromosome incorporation type vectors and artificial chromosome vectors can be used.

A marker gene may also be contained in the above vector to enable selection of transformed cells. Examples of a marker gene include URA3 and niaD, which complement the auxotrophy of hosts, and resistance genes against drugs, such as ampicillin, kanamycin or oligomycin. In addition, the recombinant vector preferably contains a promoter sequence which facilitates expression of the gene of the present invention in a host cell, or other regulation sequences (for example, an enhancer sequence, terminator sequence and polyadenylation sequence). Specific examples of such a promoter include the GAL1 promoter, the amyB promoter and the lac promoter. Further, a tag may also be added to enable purification. For example, a linker sequence is properly connected downstream of a glutaminase gene, and then 6 or more codons of nucleotide sequences encoding histidines are connected, thereby enabling purification through a nickel column.

4. Obtainment of Transformant

The transformant of the present invention can be obtained by transforming a host with the recombinant vector of the present invention. Examples of a host are not specifically limited, as long as they can produce the glutaminase of the present invention, and include yeast such as *Saccharomyces cerevisiae*, and *Zygosaccharomyces rouxii*, filamentous fungi, such as *Aspergillus sojae*, *Aspergillus oryzae* and *Aspergillus niger*, and bacteria, such as *Escherichia coli* and *Bacillus subtilis*. Transformation can be performed by any known method depending on the host to be used herein. In the case of yeast, for example, a method using lithium acetate (Methods Mol. Cell. Biol., 5, 255–269 (1995)) can be used. In the case of filamentous fungi, for example, a method using polyethylene glycol and calcium chloride (Mol. Gen. Genet., 218, 99–104 (1989)) after protoplast preparation can be used. When bacteria are used, for example, a method using electroporation (Methods Enzymol., 194, 182–187(1990)) can be used.

5. Production of Glutaminase

A method for producing the glutaminase of the present invention comprises culturing the transformant or the transductant of the present invention, and collecting glutaminase protein from the resulting culture product. A medium and a culturing method may be appropriately selected according to host type and a regulatory sequence for expression in a recombinant vector. For example, when the host is *Saccharomyces cerevisiae* and a regulatory sequence for expression is the GAL1 promoter. Microbes pre-cultured in a liquid minimal medium containing raffinose as a carbon source are diluted, inoculated and cultured in a liquid minimal medium containing galactose and raffinose as carbon sources, so as to allow the cells to produce the glutaminase of the present invention. Further, for example, when the host is *Aspergillus sojae* and a regulatory sequence for expression is the amyB promoter, for example, the cells are cultured in a liquid minimal medium containing maltose as a carbon source, so as to allow the cells to produce the glutaminase of the present invention.

Moreover, when the host is *Escherichia coli* and a regulatory sequence for expression is the lac promoter, the cells are cultured in a liquid medium containing IPTG, so that the glutaminase of the present invention can be produced. When the glutaminase of the present invention is produced within the bacteria or on the bacterial surface, the bacteria are separated from the medium and then appropriately treated, so that the glutaminase of the present invention can be obtained. For example, when the glutaminase is produced on the microbial surface of *Saccharomyces cerevisiae*, the microbial body itself is used as an enzyme agent to disrupt the microbial bodies, and non-ionic surfactant such as TRITON® X-100, TWEEN®-20 or NONIDET® P-40 is allowed to act at a low concentration. Centrifugation is then performed, and then the glutaminase of the present invention can be collected from the supernatant. When the glutaminase of the present invention is produced in the culture solution, the microbial bodies are removed by centrifugation, filtration or the like, so that the glutaminase of the present invention can be obtained. In any cases, the glutaminase of the present invention having a higher purity can be obtained by any conventional method using an ammonium sulfate fraction, various types of chromatography, alcohol precipitation, ultrafiltration or the like.

Examples of a method for measuring the titer of glutaminase include measurement method 1 which involves quantitatively determining L-glutamic acid generated by hydrolysis of L-glutamine, and measurement method 2 which involves quantitatively determining ammonia generated by enzyme reaction. A commercial kit, such as F-KIT® ammonia (Roche Diagnosis) may be employed for the measurement method 2. Measurement method 1 was employed as a method for measuring the titer of this enzyme.

Specifically, 500 µl of 0.2 M phosphate buffer (pH 7.0) and 250 µl of an enzyme solution were added to 250 µl of 2% (W/V) L-glutamine solution, the solution was allowed to react at 37° C. for 20 minutes, and then 250 µl of 0.75 N perchloric acid solution was added to the solution to stop the reaction. Then, 125 µl of 1.5 N sodium hydroxide solution was added to the solution, thereby neutralizing the reaction solution. The above reaction solution was centrifuged (10,000 r.p.m., 10 minutes). To 100 µl of the supernatant, 1.0 ml of 0.1 M hydroxylamine hydrochloride buffer solution (pH 8.0) containing 50 mM EDTA·Na, 1.0 ml of 20 mM NAD+ solution (Oriental Yeast) and 50 µl of 500 unit/ml L-glutamate dehydrogenase solution (SIGMA™) were added. Then, the solution was allowed to react at 37° C. for 30 minutes, and then absorbance at 340 nm was measured using a spectral photometer. The titer is calculated from a previously prepared calibration curve of L-glutamic acid, whereby the production amount had been previously checked, and the amount of enzyme that generates 1µ mole of glutamic acid per minute under the above conditions is defined as 1 unit (U).

In particular, the glutaminase activity of the glutaminase of the present invention is superior to all known glutaminases under high temperature conditions. Specifically, though the conversion efficiency from glutamine to pyroglutamic acid increases as temperature rises, the use of the glutaminase of the present invention enables rapid hydrolysis of glutamine into glutamic acid under high temperature. Therefore, the use of the glutaminase of the present invention enables enzyme reaction under high temperature conditions during the production process for food or the like, and prevents contamination by saprophytes, so that food flavorings that are rich in glutamic acid content can be efficiently produced.

BEST MODE FOR CARRYING OUT THE INVENTION

Figure 1:
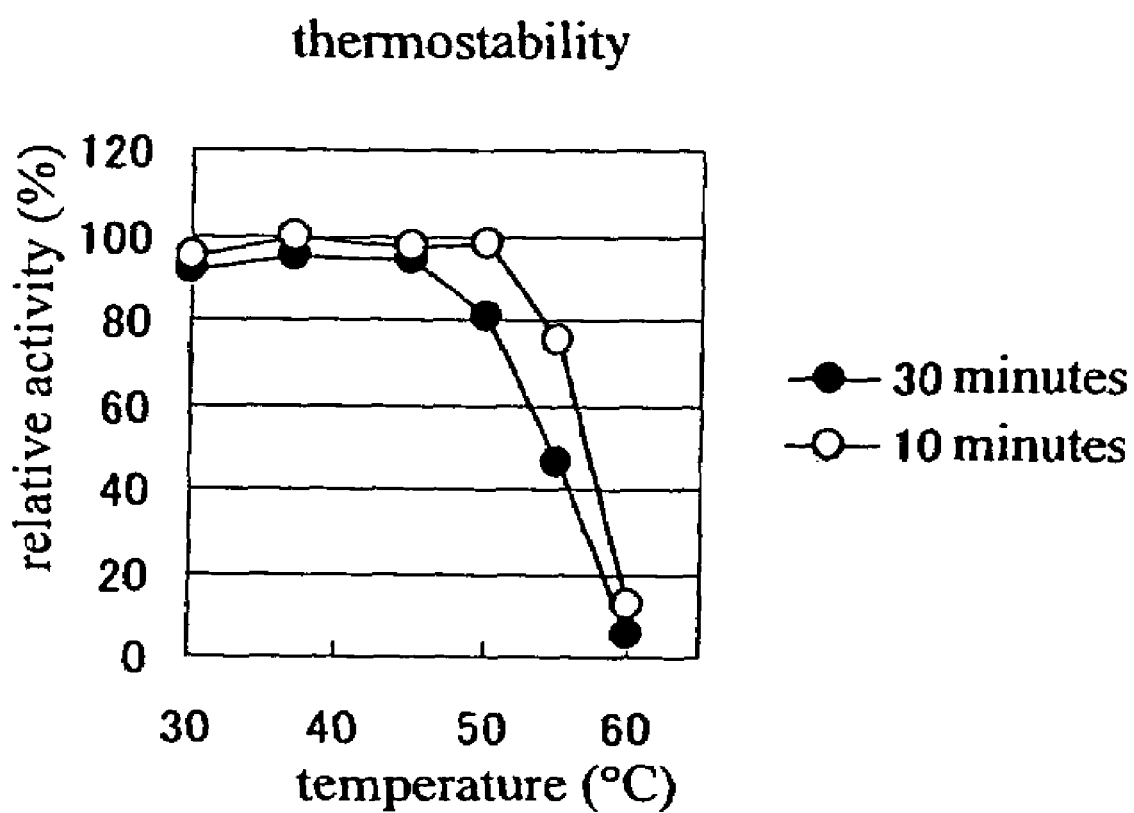
FIG. 1 is a characteristic figure representative of the thermostability of this enzyme.

The present invention will be described more specifically by the following examples. However, the present invention is not limited by these examples.

1. Cloning of Glutaminase Gene of *Aspergillus oryzae*

Approximately 100,000 conidiospores of *Aspergillus oryzae* strain RIB40 (*Aspergillus oryzae* var. *viridis* Murakami, anamorph; ATCC42149) were inoculated into 5 g of a bran medium (described above) in a 150 ml Erlenmeyer flask, and then statically cultured at 30° C. for 30 hours, thereby yielding the culture product. The culture product was put into a mortar that had been previously cooled by pouring liquid nitrogen into the mortar. After further adding liquid nitrogen into the mortar, the culture product was thoroughly crushed with a pestle that had been pre-cooled in liquid nitrogen. Total RNA was extracted from the crushed microbes by the method of Cathala et al [DNA, 2 (4): 329–335, 1983]. Furthermore, DNase I treatment was performed using a DNA-FREE™ kit (AMBION™) so that contaminating DNA was degraded. RT-PCR was performed using 1.0 µg of the obtained total RNA, as a template, and MARATHON® cDNA Amplification Kit (CLONTECH™).

Primers used for reverse transcription reaction were those attached to the kit and having an adapter sequence on the 3' side of oligo dT. Reverse transcription reaction was performed at 42° C. for 60 minutes.

Subsequently, according to the instructions attached to the kit, a cocktail containing RNaseH, DNA polymerase, DNA ligase and the like was added to the above reverse transcription reaction mixture as described above. The mixture was allowed to react at 16° C. for 90 minutes. T4 DNA polymerase was further added to the mixture, and the resulting mixture was allowed to react at 16° C. for 50 minutes, thereby synthesizing a double-stranded cDNA library.

Next, adapter DNA, DNA ligase and the like were added to the above reaction product, so that a double-stranded cDNA library having an adapter bound thereto was synthesized. Compositions of the reaction solutions and reaction conditions were respectively employed according to the instructions enclosed in the kit.

Next, primers were prepared in reference to the genome database of *Aspergillus oryzae*. Then, 5'RACE and 3'RACE were performed using the double-stranded cDNA library obtained above as a template and FIRSTCHOICE® RLM-RACE Kit (AMBION™) and MARATHON® cDNA Amplification Kit (CLONTECH™). As a result, approximately 400 bp and 700 bp amplification fragments were respectively obtained, so that expression of the gene of the enzyme was confirmed. In addition, a primer of SEQ ID NO: 3 and that of SEQ ID NO: 4 were used for 5'RACE, and a primer of SEQ ID NO: 5 and that of SEQ ID NO: 6 were used for 3'RACE. After the transcription initiation point and the transcription termination point were clarified using the RACE method, primers of SEQ ID NO: 7 and SEQ ID NO: 8 were designed. Using the double-stranded cDNA library obtained above as a template, PCR amplification was performed from a position immediately before the initiation codon on the 5' side, and to a position immediately before the termination codon on the 3' side. TAKARA EX TAQ™ DNA Polymerase (TAKARA SHUZO) was used as a thermostable DNA polymerase, and the composition of the reaction solution was prepared according to the instructions enclosed with the TAKARA EX TAQ™ polymerase.

After reaction at 94° C. for 2 minutes, the PCR reaction was performed for 30 cycles, each cycle consisting of 94° C. for 30 seconds, 55° C. for 30 seconds, and 72° C. for 2 minutes. Then, another reaction was performed at 72° C. for 5 minutes. When a part of the amplification product was subjected to 0.7% agarose gel electrophoresis, an approximately 1.8 kb band was confirmed. In addition, GENE-AMP® 5700 Sequence detection system (PE Applied Biosystems) was used as a thermal cycler, and the temperature was controlled by a calculate control method.

Next, the above amplification product was inserted into pYES2.1/V5-His-TOPO® vector using pYES2.1TOPO® TA Expression Kit (INVITROGEN™). The vector TOP10F' was then transformed into *Escherichia coli* strain ONE SHOT® (INVITROGEN™). Plasmids were extracted from the transformants using QIAPREP® spin Miniprep Kit (QIAGEN™). The plasmids were then treated using restriction enzymes, Xba I and Hind III (both produced by TAKARA SHUZO), so that the direction of the gene insertion can be confirmed. Sequencing reaction was performed using CEQ™ DTCS-Quick Start Kit (BECKMAN COULTER), and the nucleotide sequence was determined using CEQ™2000XL sequencer (BECKMAN COULTER).

As a result, DNA sequence of a 1884 bases open reading frame (ORF) represented by SEQ ID NO: 1 was obtained. This plasmid "pYESAsgahB" was deposited under FERM BP-8260 on Dec. 12, 2002 to the National Institute of Advanced Industrial Science and Technology, International Patent Organism Depository (Chuo-6, 1-1-1, Higashi, Tsukuba-shi, Ibaraki, Japan). In addition, the nucleotide sequence ranging from the initiation codon to a position immediately before the termination codon of a clone contained in pYESAsgahB is shown in SEQ ID NO: 1. The analysis of the above nucleotide sequence revealed that the DNA encodes a protein comprising 628 amino acid residues. This amino acid sequence is shown in SEQ ID NO: 2.

Furthermore, a search was conducted for sequences having high sequence homology with this amino acid sequence SEQ ID NO: 2 in a known amino acid sequence database. NCBI blastp was used for this search, and nr was designated as a database. As a result, no matched sequence was found, and the sequence having the highest sequence homology was an ORF near MEL (GenBank: CAA85738), which was a protein of the yeast *Saccharomyces cerevisiae*, having unknown functions. The sequence homology of the full length coding region was approximately 42% as determined with analytical software GENETYX™-WIN Ver. 5.0. In addition, when NCBI blastp was used, no known glutaminase was found to have high homology with the amino acid sequence represented by SEQ ID NO: 2.

Further, we searched for sequences having high sequence homology with the nucleotide sequence represented by SEQ ID NO: 1. NCBI blastn was used for this search, and nr was designated as a database. No matched sequence was found. The sequence homology of the full length coding region of the ORF near MEL (GenBank: CAA85738), which showed the highest sequence homology with the amino acid sequence as described above, was 50% and the sequence was over 1884 bases in length as determined by the analytical software GENETYX™-WIN Ver. 5.0. In addition, when the NCBI blastn was used, no known glutaminase gene was found to have high homology with the nucleotide sequence represented by SEQ ID NO: 1.

2. Expression of Glutaminase cDNA

With the plasmid pYESAsgahB described above, the protein of interest (glutaminase) can be expressed by induction using galactose. INVSc1 (INVITROGEN™, Genotype: MATa, his3Δ 1, leu2, trp1-289, ura3-52/MATα, his3Δ 1, leu2, trp1-289, ura3-52) was used as a host. The host yeast was transformed by the lithium acetate method using the above plasmid pYESAsgahB. 0.67% Yeast Nitrogenbase without amino acids (DIFCO™), 2% raffinose (Wako Pure Chemical Industries), and 0.192% Yeast Synthetic Drop-out Medium Supplement Without uracil (SIGMA™) were used in a selection medium. The lithium acetate method was performed according to "A protein experimental protocol-functional analysis-" (P63–P88 Cell Technology, separate volume: SHUJUNSHA).

Next, using the obtained transformant, protein was expressed according to the protocols enclosed in the pYES2.1TOPO® TA Expression Kit. The transformants were inoculated from colonies in 20 ml of the selection medium in a 200 ml baffle sided Erlenmeyer flask, and then the transformants were cultured by shaking at 30° C. for about 14 hours at 140 rpm, thereby preparing a seed culture. The turbidity ($OD_{600}$) of the seed culture was measured, and then the seed culture was inoculated into a medium to induce protein expression to have an initial turbidity of $OD_{600}$=0.4. A 500 ml Sakaguchi flask was used for the culture in the medium to induce protein expression, and the culture was shaken in 50 ml medium at 30° C. at 140 rpm. The medium to induce protein expression used herein was a selection medium containing 1% raffinose and 2% galactose (Wako Pure Chemical Industries) as carbon sources.

At 30 hours after the start of induction, the culture solution was centrifuged at 3000 rpm for 10 minutes, obtaining the supernatant as a fraction of extra-microbial secretory protein and the precipitation as a fraction of the microbes. An extraction buffer in an equivalent volume with the pellet (20 mM Tris-HCl (pH7.5), 1 mM EDTA, 5 mM $MgCl_2$, 50 mM KCl, 5% glycerol, 3 mM DTT, 1% protease inhibitor mix/DMSO solution (Wako Pure Chemical Industries)) was added to the fraction of the microbes for suspension, thereby preparing a suspension solution of the microbes. An equivalent volume of glass beads was added to the suspension solution, the solution was vigorously agitated using a multi-beads shocker for 30 seconds. Then, the solution was cooled in ice for 1 minute and 30 seconds. After repeating this procedure for 15 times, centrifugation at 15000 rpm was performed for 20 minutes, thereby obtaining the supernatant as a fraction of intra-microbial soluble protein and the precipitation as a fraction of the microbial residues Glutaminase activity was measured using the fraction of intra-microbial soluble protein obtained as a crude enzyme solution as described above. Table 1 shows the results. Numerical values in Table 1 denote glutaminase activity (mU/mg) per total amount of intra-microbial soluble protein at 30 hours after induction of protein expression. "Vector" denotes the transformant of plasmid pYES2.1-V5-his-TOPO®, "AsgahB" denotes the transformant of plasmid pYESAsgahB, respectively. In addition, (−) indicates that culturing was performed in a medium that contained no galactose and thus not suitable for inducing protein expression, and (+) indicates that the culture was performed in a medium that contained galactose and was suitable for inducing protein expression.

TABLE 1

| Vector (−) | Vector (+) | AsgahB (−) | AsgahB (+) |
|---|---|---|---|
| 6.1 | 5.1 | 5.1 | 123.8 |

The results shown in Table 1 revealed that the transformants of plasmid pYESAsgahB cultured in the medium for inducing protein expression showed glutaminase activity approximately 24-fold greater than that of the transformants of plasmid pYES2.1-V5-his-TOPO®. Further, it was also revealed that the transformants of plasmid pYESAsgahB showed glutaminase activity approximately 24-fold greater than that achieved by culturing in the medium that contained no galactose. As described above, it was confirmed that the gene obtained by the present invention was glutaminase gene, and it became clear that the use of this gene enables mass-production of glutaminase.

3. Optimum Temperature and Thermostability of Glutaminase

When pYES2.1TOPO® TA Expression Kit was used, V5 epitope tag and then 6×His tag were incorporated to the C-terminal site of this enzyme. Enzyme was purified from a crude enzyme solution of intra-microbial soluble fractions obtained in a manner similar to the method of the above 2 using TALON™ Purification Kit (CLONTECH™). However, the 1× Elution/Wash buffer included in the Kit was used instead of the extraction buffer to prepare the crude enzyme solution of the intra-microbial soluble fractions. The purification was performed by a method according to the protocols included in the Kit. Specifically, resin that had been previously equilibrated with 1× Elution/Wash buffer was added to the obtained crude enzyme solution. The solution was then gently agitated at 4° C. for 30 minutes to allow the enzyme to be adsorbed to the resin. The resin with the enzyme adsorbed thereto was centrifuged at 1000 rpm for 5 minutes, thereby separating into the resin and the supernatant, which represents a non-adsorbed fraction. The glutaminase activity of the crude enzyme solution and that of the non-adsorbed fraction was measured, to confirm that the enzyme was adsorbed to the resin. Subsequently, the resin with the enzyme adsorbed thereto was washed with a 10-fold volume of 1× Elution/Wash buffer, and then centrifuged at 1000 rpm for 5 minutes, which was followed by collecting the resin. After this procedure was repeated twice, the resin was suspended in 1-fold volume of 1× Elution/Wash buffer, and then the suspension was transferred into a gravity-flow column. After the resin was washed with a 5-fold volume of 1× Elution/Wash buffer, elution was performed with a 5-fold volume of 1× Elution buffer, so that an active fraction may be collected. With the procedures as described above, purified glutaminase was achieved.

The thermostability and optimum temperature of the above purified enzyme were examined.

(I) Thermostability (Heat-Stability)

The enzyme was subjected to heat treatment at 30 to 60° C. for 10 minutes or 30 minutes in 0.1 M phosphate buffer (pH 7.0), and then cooled sufficiently. Then, the activity was measured in 0.1 M phosphate buffer (pH 7.0) at 37° C. The reactivity of a sample that had not been subjected to heat treatment for 30 minutes was set as 100%, and the reactivity at each temperature was obtained as a relative value. FIG. 1 shows the results. The results shown in FIG. 1 revealed that the enzyme showed 80% or more remaining activity at 50° C. or less.

(II) Optimum Temperature

Figure 2:
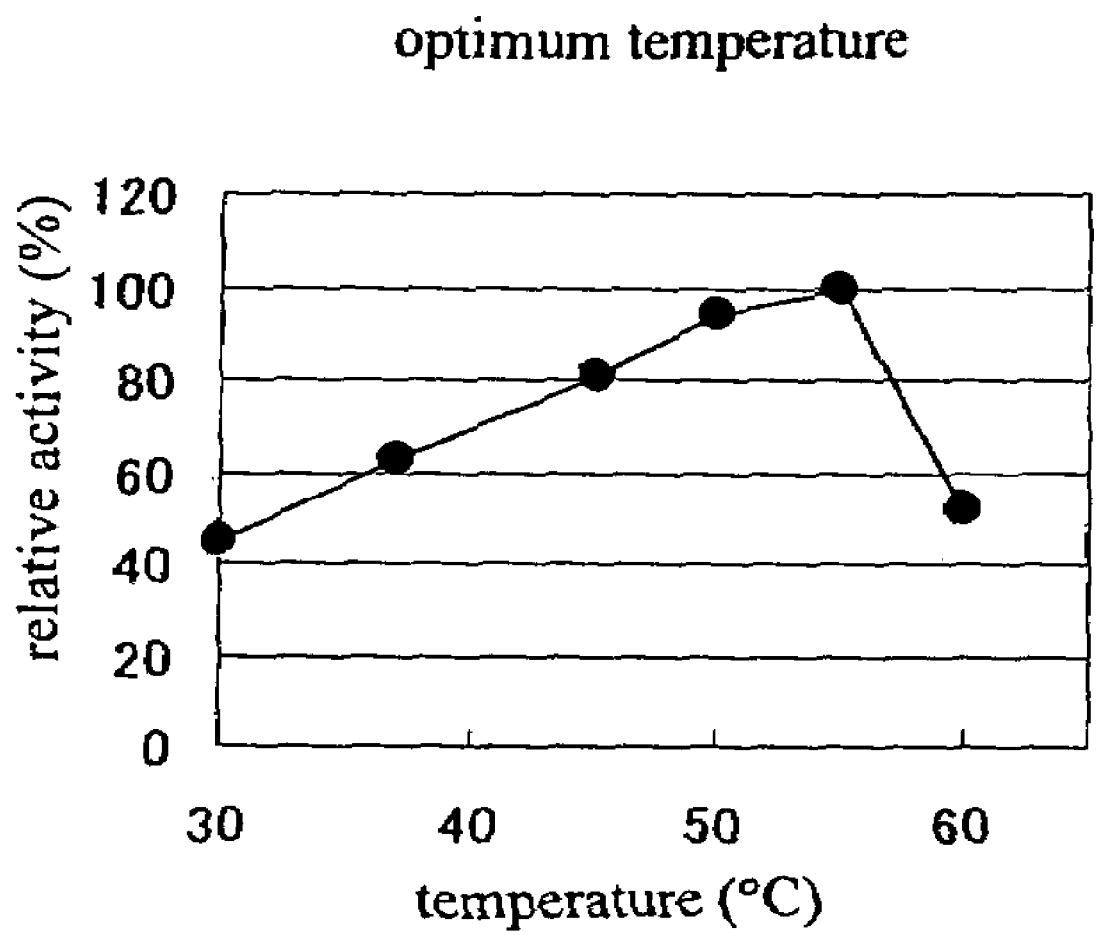
FIG. 2 is a characteristic figure representative of the optimal temperature of this enzyme.

The activity was measured in 0.1 M phosphate buffer (pH 7.0) at 30 to 60° C. With the highest value as 100%, the reactivity at each temperature was obtained as a relative value. FIG. 2 shows the results. The results shown in FIG. 2 revealed that the optimum temperature of the enzyme was 55° C.

Table 2 summarizes the optimum temperatures (FIG. 2) and thermostabilities (FIG. 1) of known glutaminases derived from koji molds, *Aspergillus oryzae* and *Aspergillus sojae*. Temperature described in the row "thermostability" in Table 2 denotes the temperature of heat treatment at which 80% or more remaining activity was shown when heat treatment was performed for the duration in the parentheses.

TABLE 2

| | The enzyme | Yano, T. et al | WO99/60104 | JP Patent Publication (Unexamined Application) No. 2000-166547 | JP Patent Publication (Unexamined Application) No. 2002-218986 |
|---|---|---|---|---|---|
| Origin | *Aspergillus oryzae* | *Aspergillus oryzae* | *Aspergillus oryzae* | *Aspergillus sojae* | *Aspergillus sojae* |
| Optimum temperature (° C.) | 55 | 37–45 | 45 | 50 | 45 |
| Thermostability (Duration of heat treatment) | 50° C. or less (30 minutes) | 37° C. or less (10 minutes) | 45° C. or less (10 minutes) | 45° C. or less (30 minutes) | 40° C. or less (30 minutes) |

The results shown in Table 2 revealed that the enzyme has a high optimum temperature and excellent thermostability compared to conventionally known glutaminases derived from the genus *Aspergillus*.

INDUSTRIAL APPLICABILITY

According to the present invention, we provided a completely novel protein, glutaminase gene, recombinant DNA and a method for producing the glutaminase. According to the present invention, it became possible to improve the above glutaminase by protein engineering. The present invention can also be used for producing enzyme for food processing, and improving microorganisms to be used for producing brewed foods Sequence Listing Free Text SEQ ID NOS: 3 to 8 are primers.

The invention claimed is:

1. An isolated nucleic acid comprising a polynucleotide sequence
encoding an amino acid sequence of SEQ ID NO: 2.

2. A recombinant nucleic acid comprising the nucleic acid of claim 1.

3. An isolated vector comprising the recombinant nucleic acid of claim 2.

4. An isolated host cell comprising the recombinant nucleic acid of claim 2.

5. The isolated host cell of claim 4, selected from a group comprising a yeast, a fungi and a bacterium.

6. A method for producing a glutaminase, comprising culturing the isolated host cell according to claim 4 in a culture medium and collecting glutaminase from said culture medium.

7. An isolated nucleic acid comprising a polynucleotide sequence
of SEQ ID NO: 1.

8. A recombinant nucleic acid comprising the nucleic acid of claim 7.

9. An isolated vector comprising the recombinant nucleic acid of claim 8.

10. An isolated host cell comprising the recombinant nucleic acid of claim 8.

11. The isolated host cell of claim 10, selected from a group comprising a yeast, a fungi and a bacterium.

12. A method for producing a glutaminase, which comprises culturing the isolated host cell according to claim 10 in a culture medium and collecting glutaminase from said culture medium.

* * * * *

UNITED STATES PATENT AND TRADEMARK OFFICE
CERTIFICATE OF CORRECTION

PATENT NO. : 7,186,540 B2 Page 1 of 1
APPLICATION NO. : 10/327388
DATED : March 6, 2007
INVENTOR(S) : Masayuki Machida et al.

It is certified that error appears in the above-identified patent and that said Letters Patent is hereby corrected as shown below:

In column 21, on line 41, replace the paragraph starting with the words "1. An isolated nucleic acid comprising . . . " with the following paragraph:

-- 1. An isolated nucleic acid comprising a polynucleotide sequence encoding the amino acid sequence of SEQ ID NO: 2. --

In column 21, on line 56, replace the paragraph starting with the words "7. An isolated nucleic acid comprising . . . " with the following paragraph:

-- 7. An isolated nucleic acid comprising the polynucleotide sequence of SEQ ID NO: 1. --

Signed and Sealed this

First Day of May, 2007

JON W. DUDAS
*Director of the United States Patent and Trademark Office*

```
                             SEQUENCE LISTING

<160> NUMBER OF SEQ ID NOS: 8

<210> SEQ ID NO 1
<211> LENGTH: 1884
<212> TYPE: DNA
<213> ORGANISM: Aspergillus oryzae RIB40

<400> SEQUENCE: 1
atgctctcct ctgttctcct tgtcctcttc tcagcggccg tgggggcaaa gaccgtgccc      60
aacggccaaa cactcaccct caacggcata ccctactatc tcagtgggat cccgatttcg     120
aatttctcac ataatgtttt cgataaagca agcaacgatg tcgatatctt ccctttaca     180 gtcatccaga cttctagcac cgttcatagt agctttctga gtgaaacagt tgccaatttt     240
acccagcagg atgacgtgtt ccaacctgcg tttcttcaga ccgtctattt gacttcttct     300
gttgaggcgt cgcaaatcga cgaactgtct ggcagcgaag ctttgcacca gtttgacaat     360
aagatgttcc taaccgaatc tgatgcttcc ttgtctacgc cccttccgaa tggaccttat     420
tttgcttccg cccgcacagg acacattttc agagcctatc gtctctactc tgatgactct     480
ttggcgttca tctcggccgc tattagcgat gagagtggtg gtttcattcc tatgactgga     540
gttacagagg gcgtcatgac gaaaaatgtc gctgtcccat cccgtctcta ctacaccct      600 actgctgaaa agcctttagc tggtttccgg ctggccgtga aggatatatt ccacattaag     660
ggtcttagaa ccagtggtgg aagccgtgcg tactactacc tctacgatga gcagaatgtt     720
accactccct ctgtgcaacg gctctttgac ctgggtgccg taatggtcgg aaaggtgggc     780
actgttcaat cgccaatggt tgatcgtcct actgcggact gggtcgatct gcactgtcca     840
ttcaaccccc gagggacgg atatcaatat cccagtggct cctcgtctgg ttcgggtgct     900
gccatcgccg cgtatgaatg gttagatctg gctattggca gtgacacggg tggttccatg     960
cgcggacctg ccggtgtgca gggtatctat ggtaatcggc catcaactgg ggctatcact    1020
ttagagcatg ccttgccact ctcgcctcca ctcgatacag ccggtatgtt cgcacgaagc    1080
gcgtctttat ggtcaaagac cgtccaagcc tggtaccca acttcaaccg cagctatcca    1140
tcccacccca aacagctcta cctctctcac agcaactggg acgagtccac cgcacccgaa    1200
gcaaacgaac atctggaaac attcatgcag agactcgaag atttcctgga tacaaatcgc    1260
acaatcgtca acgtcacaga acgttggtcc gaaacccaca actcaccctc tttgatcaac    1320
ctcctgaaca caacctacgc ctacctagtc ggcgtcggcc aatggaataa tctcgccaaa    1380
ggcttcttcg cagactacgc ccaatcccac gacggccgtc gcccattcat caatcccggt    1440
cccttggccc gctgggaatg gggccaagca aacggtggaa acgcatccta cgacgccgcc    1500
ctgcataaca tgactgtctt ccagagactgg tggtcgacgt ccggatacgg acgttctgat    1560
gatgattctt gctcggaagg tatcttcgta cacgcctggg ccaccggagc agcagactac    1620
cgtaaccggt acttcaaccc tcctggtccc ccgttcggat tcacagacga cgctatcgcc    1680
gttttcgcgg gcgcgcctga agttgttgtc ccattgggcg agtcgcctta taacagtacc    1740
atcacgttgc acgaggagta tctccctgtt tcgatcggct tgcagatggc tagaggctgc    1800
gatcgggcac ttgctgagtt ggtggatgat ctaggcaagg cagggatttt gaagcctgtt    1860
tctgcgggct cgagattata ttct                                           1884
```

<210> SEQ ID NO 2
<211> LENGTH: 628
<212> TYPE: PRT
<213> ORGANISM: Aspergillus oryzae RIB40

<400> SEQUENCE: 2

```
Met Leu Ser Ser Val Leu Leu Val Leu Phe Ala Ala Val Gly Ala
 1               5                  10                  15

Lys Thr Val Pro Asn Gly Gln Thr Leu Thr Leu Asn Gly Ile Pro Tyr
                 20                  25                  30

Tyr Leu Ser Gly Ile Pro Ile Ser Asn Phe Ser His Asn Val Phe Asp
             35                  40                  45

Lys Ala Ser Asn Asp Val Asp Ile Phe Pro Phe Thr Val Ile Gln Thr
         50                  55                  60

Ser Ser Thr Val His Ser Ser Phe Leu Ser Glu Thr Val Ala Asn Phe
 65                  70                  75                  80

Thr Gln Gln Asp Asp Val Phe Gln Pro Ala Phe Leu Gln Thr Val Tyr
                 85                  90                  95

Leu Thr Ser Ser Val Glu Ala Ser Gln Ile Asp Glu Leu Ser Gly Ser
            100                 105                 110

Glu Ala Leu His Gln Phe Asp Asn Lys Met Phe Leu Thr Glu Ser Asp
        115                 120                 125

Ala Ser Leu Ser Thr Pro Leu Pro Asn Gly Pro Tyr Phe Ala Ser Ala
    130                 135                 140

Arg Thr Gly His Ile Phe Arg Ala Tyr Arg Leu Tyr Ser Asp Asp Ser
145                 150                 155                 160

Leu Ala Phe Ile Ser Ala Ile Ser Asp Glu Ser Gly Gly Phe Ile
                165                 170                 175

Pro Met Thr Gly Val Thr Glu Gly Val Met Thr Lys Asn Val Ala Val
            180                 185                 190

Pro Ser Arg Leu Tyr Tyr Thr Pro Thr Ala Glu Lys Pro Leu Ala Gly
        195                 200                 205

Phe Arg Leu Ala Val Lys Asp Ile Phe His Ile Lys Gly Leu Arg Thr
    210                 215                 220

Ser Gly Ser Arg Ala Tyr Tyr Leu Tyr Asp Glu Gln Asn Val
225                 230                 235                 240

Thr Thr Pro Ser Val Gln Arg Leu Phe Asp Leu Gly Ala Val Met Val
                245                 250                 255

Gly Lys Val Gly Thr Val Gln Phe Ala Asn Gly Asp Arg Pro Thr Ala
            260                 265                 270

Asp Trp Val Asp Leu His Cys Pro Phe Asn Pro Arg Gly Asp Gly Tyr
        275                 280                 285

Gln Tyr Pro Ser Gly Ser Ser Gly Ser Gly Ala Ala Ile Ala Ala
    290                 295                 300

Tyr Glu Trp Leu Asp Leu Ala Ile Gly Ser Asp Thr Gly Gly Ser Met
305                 310                 315                 320

Arg Gly Pro Ala Gly Val Gln Gly Ile Tyr Gly Asn Arg Pro Ser Thr
                325                 330                 335

Gly Ala Ile Thr Leu Glu His Ala Leu Pro Leu Ser Pro Leu Asp
            340                 345                 350

Thr Ala Gly Met Phe Ala Arg Ser Ala Ser Leu Trp Ser Lys Thr Val
        355                 360                 365

Gln Ala Trp Tyr Pro Asn Phe Asn Arg Ser Tyr Pro Ser His Pro Lys
```

```
                  370                 375                 380
Gln Leu Tyr Leu Ser His Ser Asn Trp Asp Ser Thr Ala Pro Glu
385                 390                 395                 400

Ala Asn Glu His Leu Glu Thr Phe Met Gln Arg Leu Glu Asp Phe Leu
                405                 410                 415

Asp Thr Asn Arg Thr Ile Val Asn Val Thr Glu Arg Trp Ser Glu Thr
            420                 425                 430

His Asn Ser Pro Ser Leu Ile Asn Leu Leu Asn Thr Thr Tyr Ala Tyr
        435                 440                 445

Leu Val Gly Val Gly Gln Trp Asn Asn Leu Ala Lys Gly Phe Phe Ala
450                 455                 460

Asp Tyr Ala Gln Ser His Asp Gly Arg Arg Pro Phe Ile Asn Pro Gly
465                 470                 475                 480

Pro Leu Ala Arg Trp Glu Trp Gly Gln Ala Asn Gly Gly Asn Ala Ser
                485                 490                 495

Tyr Asp Ala Ala Leu His Asn Met Thr Val Phe Arg Asp Trp Trp Ser
            500                 505                 510

Thr Ser Gly Tyr Gly Arg Ser Asp Asp Ser Cys Ser Glu Gly Ile
        515                 520                 525

Phe Val His Ala Trp Ala Thr Gly Ala Ala Asp Tyr Arg Asn Arg Tyr
530                 535                 540

Phe Asn Pro Pro Gly Pro Pro Phe Gly Phe Thr Asp Asp Ala Ile Ala
545                 550                 555                 560

Val Phe Ala Gly Ala Pro Glu Val Val Val Pro Leu Gly Glu Ser Pro
                565                 570                 575

Tyr Asn Ser Thr Ile Thr Leu His Glu Glu Tyr Leu Pro Val Ser Ile
            580                 585                 590

Gly Leu Gln Met Ala Arg Gly Cys Asp Arg Ala Leu Ala Glu Leu Val
        595                 600                 605

Asp Asp Leu Gly Lys Ala Gly Ile Leu Lys Pro Val Ser Ala Gly Ser
    610                 615                 620

Arg Leu Tyr Ser
625

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:Primer DNA

<400> SEQUENCE: 3
tctgaaaatg tgtcctgtgc gggcggaagc                                   30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Primer DNA

<400> SEQUENCE: 4
attgtcaaac tggtgcaaag cttcgctgcc                                   30

<210> SEQ ID NO 5
<211> LENGTH: 34
<212> TYPE: DNA
<213> ORGANISM: Artificial Sequence
```

-continued

```
<220> FEATURE:
<223> OTHER INFORMATION: Description of Artificial Sequence:Primer DNA

<400> SEQUENCE: 5
aaagagctca aaatgctctc ctctgttctc cttg                          34

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:Primer DNA

<400> SEQUENCE: 6
tctcacagca actgggacg agtccac                                   26

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:Primer DNA

<400> SEQUENCE: 7
aaagagctca aaatgctctc ctctgttctc cttg                          34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Primer DNA

<400> SEQUENCE: 8
agaatataat ctcgagcccg cagaaacagg                               30
```